United States Patent [19]

Broggi et al.

[11] 4,414,387

[45] Nov. 8, 1983

[54] CEPHAPIRIN ACETYLCYSTEINATE HAVING ANTIBACTERIAL ACTIVITY

[76] Inventors: Renato Broggi, Via Bacchiglione 21, 20139 Milan; Marco Falciani, Via De Ruggiero 85, 20142 Milan, both of Italy

[21] Appl. No.: 377,837

[22] Filed: May 13, 1982

[51] Int. Cl.$^3$ ............................................. C07D 501/34
[52] U.S. Cl. ........................................................ 544/28
[58] Field of Search ........................................... 544/28

[56] References Cited

U.S. PATENT DOCUMENTS

| | | | |
|---|---|---|---|
| 3,105,005 | 9/1963 | Cannon et al. | 546/347 |
| 3,422,100 | 1/1969 | Crast et al. | 544/28 |
| 3,503,967 | 3/1970 | Silvestri et al. | 544/28 |
| 3,578,661 | 5/1971 | Hauraner et al. | 544/28 |

OTHER PUBLICATIONS

Cavallito, Chemical Abstracts, vol. 41 (1947) 94c.
Gottschalk et al., Chemical Abstracts, vol. 73 (1970) 75236x.

*Primary Examiner*—Paul M. Coughlan, Jr.
*Attorney, Agent, or Firm*—Oblon, Fisher, Spivak, McClelland & Maier

[57] ABSTRACT

Cephapirin acetylcysteinate having antibacterial activity. Said salt is obtained by reacting an aqueous solution of cephapirin with an aqueous solution of acetylcysteine. To isolate the salt, the aqueous solution is submitted to lyophilization.

1 Claim, No Drawings

CEPHAPIRIN ACETYLCYSTEINATE HAVING ANTIBACTERIAL ACTIVITY

The present invention relates to cephapirin acetylcysteinate having antibiotic activity.

Cephapirin is a well known antibiotic, which is described in U.S. Pat. No. 3,422,100 and in Japanese Patent publication No. 44-26107.

Cephapirin is usually administered parenterally as its sodium salt.

It is well known that sodium salts of this kind of antibiotics, and in particular of cephapirin, are painful on administration by injection.

It is an object of the present invention to provide a new salt of cephapirin, which are injectable without inducing painful reactions when administered.

It is another object of the present invention to provide a new salt of cephapirin which increases the absorption of the antibiotic substance and which, when absorbed by organism, is able to give and to join with the antibiotic activity which the peculiar to cephapirin its own specific activity, which may have some interest from the pharmacological point of view.

Said and other objects are attained by means of the salification of cephapirin with acetylcysteine.

To obtain that salification cephapirin is reacted in aqueous solution and at room temperature with an aqueous solution of acetylcysteine, the cephapirin salt being isolated from the aqueous solution by lyophilization.

In order that this invention may be readily available to and understood by those skilled in the art, a method of preparing the salt which is the object of the present invention is described in the following example which is given merely as as illustration of the present invention.

EXAMPLE

Cephapirin acetylcysteinate having formula

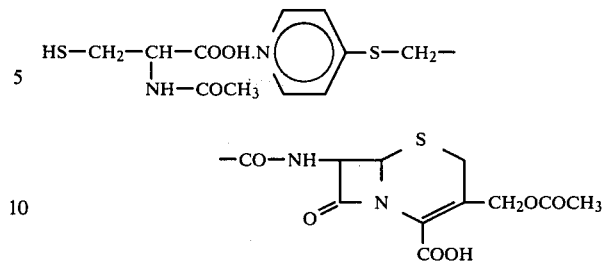

Water (500 ml) and cephapirin as acid (42. g, 0.1 mole) were charged in a reaction vessel. After cooling at 0° C., an aqueous solution containing 16.3 g (0.1 mole) of acetylcysteine was added. A complete dissolution was obtained; the resultant pH was 2.1. The mixture was allowed to react for 1 hour; then carbon (3 g) was added. The resultant solution was filtered through filter plates, poured into a tray till a 1 cm layer was obtained and subjected to prefreezing.

At −40° C. solution was completely frozen and was lyophylized. Lyophilization was finished in 36 hours.

The resultant material was screened and cephapirin acetylcysteinate (55.6 g) was obtained.

KF 1%.

TLC single product.

$[\alpha]_D$ (c=1, H$_2$O):+118°.

Microbiological titer=707 mcg/mg as cephapirin as acid.

What we claim is:

1. Cephapirin acetylcysteinate having formula

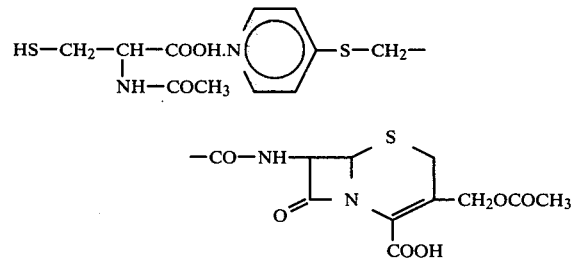

* * * * *